US010101416B2

(12) United States Patent
Bouleau et al.

(10) Patent No.: US 10,101,416 B2
(45) Date of Patent: Oct. 16, 2018

(54) METHOD AND DEVICE FOR CONTROLLING THE TEMPERATURE OF A FLOW OF FLUID INTENDED TO BE USED BY AN NMR ANALYSIS PROBE, AND CORRESPONDING NMR ANALYSIS SYSTEM (71) Applicant: COMMISSARIAT A L'ENERGIE ATOMIQUE ET AUX ENERGIES ALTERNATIVES, Paris (FR)

(72) Inventors: Eric Bouleau, Sassenage (FR); Pierre Saint-Bonnet, La Murette (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 330 days.

(21) Appl. No.: 15/047,203

(22) Filed: Feb. 18, 2016

(65) Prior Publication Data
US 2016/0245885 A1 Aug. 25, 2016

(30) Foreign Application Priority Data

Feb. 19, 2015 (FR) ...................................... 15 51384

(51) Int. Cl.
*G01R 33/34* (2006.01)
*G01R 33/30* (2006.01)
(Continued)

(52) U.S. Cl.
CPC ......... *G01R 33/3403* (2013.01); *G01N 24/08* (2013.01); *G01R 33/30* (2013.01);
(Continued)

(58) Field of Classification Search
CPC .. G01R 33/30; G01R 33/31; G01R 33/34015; G01R 33/3403; G01R 33/34092; G01N 24/08
See application file for complete search history.

(56) References Cited

U.S. PATENT DOCUMENTS 5,202,633 A * 4/1993 Doty .................... G01R 33/307
324/321
7,288,939 B1 10/2007 Barbara et al.
(Continued)

FOREIGN PATENT DOCUMENTS

FR 2 983 959 A1 6/2013

OTHER PUBLICATIONS

Martin et al. "Variable temperature system using vortex tube cooling and fiber optic temperature measurement for low temperature magic angle spinning NMR", Journal of Magnetic Resonance, vol. 168, No. 2, Mar. 27, 2004, pp. 202-209; cited in the French Search Report.

(Continued)

*Primary Examiner* — Gregory H Curran
(74) *Attorney, Agent, or Firm* — Westerman, Hattori, Daniels & Adrian, LLP (57) ABSTRACT The method comprises an initial cooling step (E0) during which the temperature (T_ECH) of the heat exchanger (30) is lowered and, at the same time, the flow rate of the said first flow ($FL_S$) is set to an initial flow rate. Following the initial cooling step (E0), an operation of circulating the first flow ($FL_S$) is initiated (E1) and during this the said first flow ($FL_S$) passes through a heat exchange (30) at a first flow rate which is higher than the initial flow rate. The initial flow rate of the first flow may be set to zero or to a value set so that the pressure inside the said circuit is greater than or equal to the pressure outside the said circuit.

25 Claims, 5 Drawing Sheets

(51) Int. Cl.
*G01R 33/31* (2006.01)
*G01N 24/08* (2006.01)

(52) U.S. Cl.
CPC ....... *G01R 33/31* (2013.01); *G01R 33/34015* (2013.01); *G01R 33/34092* (2013.01)

(56) References Cited

U.S. PATENT DOCUMENTS

| | | |
|---|---|---|
| 2010/0321018 A1 | 12/2010 | Takegoshi et al. |
| 2015/0153427 A1* | 6/2015 | Garside .................... F25B 9/00 324/318 |
| 2015/0177341 A1 | 6/2015 | De Paepe et al. |

OTHER PUBLICATIONS

French Search Report and Written Opinion dated Dec. 14, 2015 issued in counterpart application No. FR1551384; w/ English partial translation and partial machine translation (15 pages).

* cited by examiner

METHOD AND DEVICE FOR CONTROLLING THE TEMPERATURE OF A FLOW OF FLUID INTENDED TO BE USED BY AN NMR ANALYSIS PROBE, AND CORRESPONDING NMR ANALYSIS SYSTEM

The present invention relates to a method for controlling the temperature of a flow of fluid intended to be used by a nuclear magnetic resonance (NMR) analysis probe and referred to as "first flow", and to a corresponding control device. The invention also relates to a method for operating an NMR analysis system and to a corresponding NMR analysis system.

A nuclear magnetic resonance (NMR) analysis system comprises an NMR analysis probe, a circuit for circulating a flow of fluid intended to be used by the probe and a device for controlling the temperature of the flow intended for the probe, such as a cryostat.

The probe comprises a sample holder intended to contain a sample of substance that is to be analysed. During operation, the sample holder is spun in a static magnetic field and exposed to a second magnetic field perpendicular to the first. The second magnetic field may be produced by a radiofrequency coil. In return, the coil receives a signal which is analysed in order to obtain information about the sample. The flow of fluid used by the probe may have several functions, in particular the following functions:
- that of spinning the sample holder, for example by turning a turbine that drives a rotor, or spin module that incorporates the sample holder;
- that of raising the sample to a desired temperature belonging to a range of temperatures suited to creating NMR analysis spectra, for example between 300K and 8K;
- that of creating a bearing to support or guide the rotor in part of the stator.

The fluid used by the probe is, for example, helium or nitrogen. It is supplied by a source such as a cylinder of pressurized fluid (helium or nitrogen). During operation, the fluid is made to circulate in a circuit corresponding to a closed loop, which notably incorporates the probe and the device for controlling the temperature of the flow of fluid intended for the probe. The flow of fluid intended for the probe may be split, upstream of the probe, into a number of distinct flows respectively intended to perform the various functions mentioned previously.

The heat control operation applied to the flow intended for the probe is aimed at setting the temperature of this flow. It involves an exchange of heat between the flow intended for the probe and a flow of a coolant, referred to as « cryogenic flow », within a heat exchanger, so as to cool the flow intended for the probe. The cryogenic flow supplies cold from an external cryogenic fluid cold source. It circulates through the exchanger at a given flow rate. In general, the flow rate of the cryogenic flow is fixed at a maximum value.

The circuit for the circulation of the flow intended to be used by the probe is suited to collecting this flow as it leaves the probe and then circulating it through the heat exchanger, before guiding it once again towards the probe.

The rotational frequency at which the sample holder spins is dependent on the flow rate of the flow used by the probe. In order to increase this rotational frequency in order to refine the measurement of the signal, the flow rate of the flow intended for the probe needs to be increased. Because the flow rate of the cryogenic flow is fixed (generally equal to the maximum flow rate), increasing the flow rate of the flow intended for the probe has the effect of increasing the plateau or equilibrium temperature of this flow.

Figure 1:
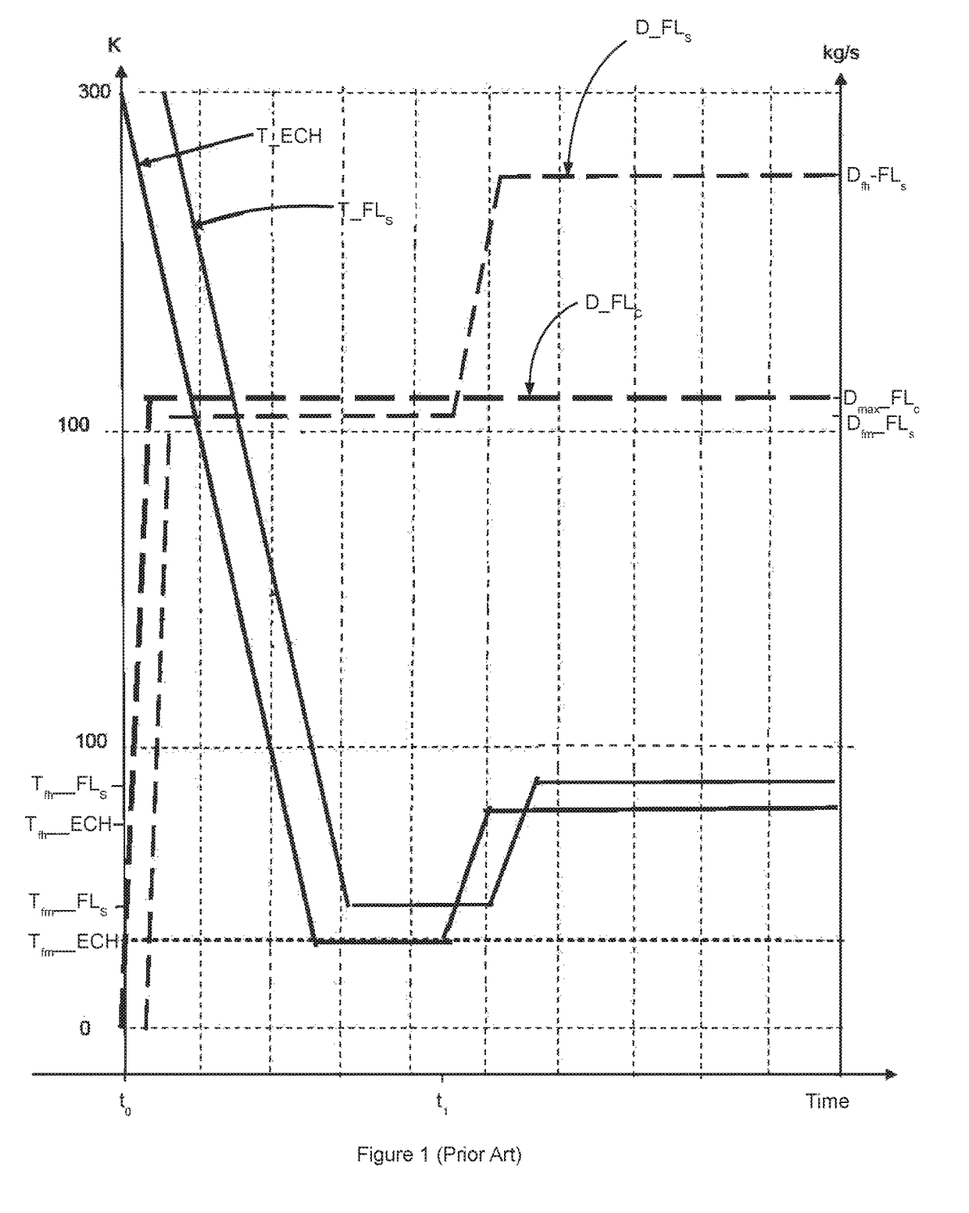
FIG. 1, by way of illustrative example, depicts the evolutions with respect to time of various physical parameters, during operation of an NMR analysis system of the prior art

FIG. 1, by way of illustrative example, depicts the evolutions with respect to time of various physical parameters, during operation of an NMR analysis system of the prior art. The physical parameters depicted comprise:
- the temperature $T\_FL_S$ and the flow rate $D\_FL_S$ of the flow intended for the probe $FL_S$;
- the flow rate $D\_FL_C$ of the cryogenic flow $FL_C$,
- the temperature $T\_ECH$ of the heat exchanger.

From the instant $t_0$ at which the NMR analysis system starts, the two flows $FL_C$ and $FL_S$ are made to circulate at the same time, or substantially at the same time, through the heat exchanger. The flow rate of the cryogenic flow $D\_FL_C$ increases rapidly until it reaches a desired value corresponding for example to a maximum flow rate $D_{max\_}FL_C$ for the cryogenic flow $FL_C$, then remains stable in the next part of the operation of the analysis system. In parallel, the flow rate $D\_FL_S$ of the probe flow is rapidly increased until it reaches a first desired flow rate $D_{fm\_}FL_S$ corresponding to a medium rotational frequency of the sample holder of the NMR analysis probe and then remains stable. Following the start, the temperature $T\_FL_S$ of the flow for the probe $FL_S$ decreases progressively, through exchange of heat with the cryogenic flow $FL_C$, and stabilizes at a first equilibrium value $T_{fm\_}FL_S$, forming a first plateau. At the same time, temperature $T\_ECH$ of the exchanger also decreases until it reaches a first equilibrium value $T_{fm\_}ECH$ forming a first plateau (slightly below the first plateau relating to the flow $FL_S$). These first temperature plateaus relating respectively to the flows $FL_S$ and $FL_C$ correspond to thermal equilibrium between these two flows $FL_C$ and $FL_S$ which have respective flow rates $D_{max\_}FL_C$ and $D_{fm\_}FL_S$ and pass through the heat exchanger, for a medium rotational frequency $f_m$ of the probe sample holder.

From an instant $t_1$ onwards, the flow rate $D\_FL_S$ is increased sharply until it reaches a second flow rate $D_{fh\_}FL_S$, higher than the first and corresponding to a high rotational frequency of the sample holder of the NMR analysis probe and then remains stable. Following the increase in the flow rate $D\_FL_S$, the temperature $T\_FL_S$ of the flow of the probe $FL_S$ increases progressively and stabilizes at a second equilibrium value $T_{fh\_}FL_S$, forming a second plateau. At the same time, the temperature $T\_ECH$ of the exchanger also increases until it reaches a second equilibrium value $T_{fh\_}ECH$, forming a second plateau (slightly below the second plateau relating to the flow $FL_S$). These second thermal plateaus relating respectively to the flows $FL_C$ and $FL_S$ correspond to thermal equilibrium between the two flows $FL_C$ and $FL_S$ which have respective flow rates $D_{max\_}FL_C$ and $D_{fh\_}FL_S$ and pass through the heat exchanger, for a high rotational frequency of the probe sample holder.

It must be emphasized that the second thermal plateaus relating to a high rotational frequency of the probe are higher than the first thermal plateaus relating to a medium rotational frequency of the probe. Definitively, with the system of the prior art, it is necessary to accord preference either to the rotational frequency, or to the operating temperature of the probe. Typically, the probe can be used either at very low operating temperatures (for example below 20K) at a medium rotational frequency (for example of the order of 5 kHz), or at a higher operating temperature (for example higher than 40K) with a high rotational frequency (for example of the order of 15 to 20 kHz).

The present invention seeks to improve the situation.

To this end, the invention relates to a method for controlling the temperature of a first flow of fluid intended to be used by a nuclear magnetic resonance analysis probe to spin a sample holder of the probe at a given rotational frequency dependent on a flow rate of the flow, comprising an operation of circulating the first flow, during which operation the said first flow passes through a heat exchanger at a first flow rate, characterized in that it comprises an initial cooling step during which the temperature of the heat exchanger is lowered and, at the same time, the flow rate of the said first flow is set to an initial flow rate which is lower than the first flow rate and, following the said initial cooling step, the operation of circulating the first flow at the first flow rate is initiated.

In one particular embodiment, the initial flow rate of the first flow is set to zero.

In one particular alternative form of the embodiment, with the first flow circulating through a circuit, the initial flow rate of the said first flow is set to a value set such that the pressure inside the said circuit is greater than or equal to the pressure outside the said circuit. By virtue of that, a slight overpressure can be created in the circuit, making it possible to avoid the ingress of external contaminants into the circuit.

The initial cooling step makes it possible to cool the heat exchanger before initiating the circulation of the first flow at the first flow rate. Because the exchanger has a certain mass and therefore a certain thermal inertia it, at the end of the initial cooling step, constitutes a reservoir of thermal energy, of the cold reservoir type, capable of intensifying the cooling of the flow intended for the probe just after it has begun to circulate at the first flow rate through the exchanger. The result of this is that the temperature of the flow intended for the probe drops below its equilibrium temperature corresponding to the set first circulation flow rate before rising again to this equilibrium temperature when the first flow is already circulating at the desired flow rate. The first flow rate at which the first flow circulates can be set to a high level corresponding to a high rotational frequency of the probe. By virtue of the invention, the temperature of the first flow, which circulates at a desired first flow rate, is lowered to a very low value which is below the thermal equilibrium temperature of the first flow. It is therefore possible to obtain both a low temperature of the first flow intended to be used by the probe (below its equilibrium temperature) and a high flow rate corresponding to a high rotational frequency of the probe sample holder Advantageously, during the initial cooling step, the temperature of the heat exchanger is lowered to a low value which is lower than an equilibrium value reached after the first flow circulation at the first flow rate.

In one particular embodiment, during the initial step, a second flow of a coolant is circulated through the heat exchanger at a flow rate such as a maximum flow rate of the said cooling flow Advantageously, during the initial step, the temperature of the exchanger is lowered to a low value which corresponds to a minimum equilibrium temperature of the heat exchanger through which the second cooling flow passes.

According to a first aspect of the invention, following the triggering of the operation of circulating the first flow, with the first flow rate of the said first flow set to a desired value, the evolution of the temperature of the first flow with respect to time comprises in succession a first phase of lowering the said temperature, a transient second phase comprising a raising of the said temperature to an equilibrium value, and an equilibrium third phase in which the said temperature is stable and equal to the equilibrium value, the said transient phase being of a duration that is set such as to allow the probe to create an NMR spectrum of a sample. During the transient phase, the temperature of the first flow passes through a temperature range which is below the equilibrium temperature of the first flow, even though the flow rate at which this first flow is circulating has already been set to a desired value, for example a value corresponding to a high rotational frequency of the probe sample holder.

According to a second aspect of the invention, the first flow, circulating at the first flow rate, passes through a heating module and the heating power of the said module is raised to a high value then decreased so that the temperature of the first flow is temporarily stable for part of the transient phase, notably for a first part of the transient phase. By virtue of that, a stable thermal plateau is created at a low value for the temperature of the first flow even though the circulation of this first flow has already been set to the first flow rate. Such a thermal plateau is highly advantageous when carrying out an NMR analysis.

Advantageously, the circulating first flow passes through the heating module downstream of the heat exchanger in the direction in which the said first flow circulates. The heating module may comprise an electrical resistance.

Advantageously also, the said first flow rate of the first flow is set to a value corresponding to a frequency greater than or equal to a limit rotational frequency, notably greater than or equal to 10 kHz.

The invention also relates to a method of operating a nuclear magnetic resonance analysis system comprising a probe for the nuclear magnetic resonance analysis of a sample, a circuit for circulating a first flow of fluid intended to be used by the said probe and a device for controlling the temperature of the said first flow comprising a heat exchanger, characterized in that the temperature of the first flow is controlled by the said control device by implementing the steps of the control method as previously defined.

In a first embodiment, with the temperature of the first flow controlled by the control method as previously defined, the probe creates an NMR spectrum of a sample during the said transient phase.

In a second embodiment, with the temperature of the first flow controlled by the control method as previously defined, the probe creates an NMR spectrum of a sample when the temperature of the first flow is temporarily stable during part of the transient phase.

The invention also relates to a device for controlling the temperature of a first flow of a fluid intended to be used by a nuclear magnetic resonance analysis probe to spin a sample holder at a rotational frequency dependent on the flow rate of the flow, incorporating at least one heat exchanger through which the first flow is intended to circulate at a first flow rate, characterized in that it comprises a command module designed to command an initial drop in the temperature of the heat exchanger and at the same time set the flow rate of the first flow to an initial flow rate lower than the first flow rate, then initiate circulation of the first flow through the exchanger at the first flow rate.

In one embodiment, the command module is designed to set the initial flow rate to zero.

In an alternative form of embodiment, with the first flow circulating through a circuit, the command module is designed to set the initial flow rate of the said first flow to a value that is set in such a way that the pressure inside the said circuit is greater than or equal to the pressure outside the said circuit.

This device advantageously comprises all or some of the following additional features:
  the heat exchanger is designed to have passing through it
    a second flow of a coolant and the command module is
    designed to initially command the cooling second flow
    to circulate at a flow rate such as a maximum flow rate of the said cooling flow, so as to obtain the initial drop in temperature of the exchanger;

the command module is designed to command an initial drop in the temperature of the exchanger down to a low value which corresponds to a minimum equilibrium temperature of the heat exchanger through which the second flow passes, before initiating the circulation of the first flow at the first flow rate;

it comprises a heating module intended to supply a thermal power to the first flow and the command module is designed to operate the heating module in such a way that the thermal power provided is at a maximum after the initiation of the circulation of the first flow at the first flow rate and then decreases in a suitable way so that the temperature of the first flow is temporarily stable;

the heating module is positioned downstream of the heat exchanger in the direction of circulation of the first flow;

the heating module comprises an electrical resistance.

The invention also relates to a nuclear magnetic resonance analysis system comprising a probe for the nuclear magnetic resonance analysis of a sample, a circuit for the circulation of a first flow of fluid intended to be used by the said probe and a device for controlling the temperature of the first flow as previously defined.

According to a first embodiment, the NMR analysis system comprises a command module designed to command the creation of a spectrum by the probe after the circulation of the first flow at the first flow rate has been initiated during a transient phase subsequent to an initial drop in the temperature of the first flow to a low value and prior to a phase of equilibrium of the temperature of the flow intended for the probe at a value higher than the said low value.

According to a second embodiment, the NMR analysis system comprises a device for controlling the temperature of the first flow as previously defined and the command module is designed to command the creation of a spectrum by the probe when the temperature of the first flow is temporarily stable during the said transient phase.

The invention will be better understood from the following description of a method for controlling the temperature of a flow of fluid intended to be used by an NMR analysis probe, referred to as a "first flow", and of a method of operating an NMR analysis system, according to various embodiments of the invention, and of a corresponding control device and a corresponding NMR analysis system, with reference to the attached drawings in which.

For the sake of clarity, in the various figures, elements in the various embodiments, alternative forms and/or exemplary embodiments of the invention which are analogous or correspond to one another bear the same references, unless specifically indicated to the contrary.

Figure 4:
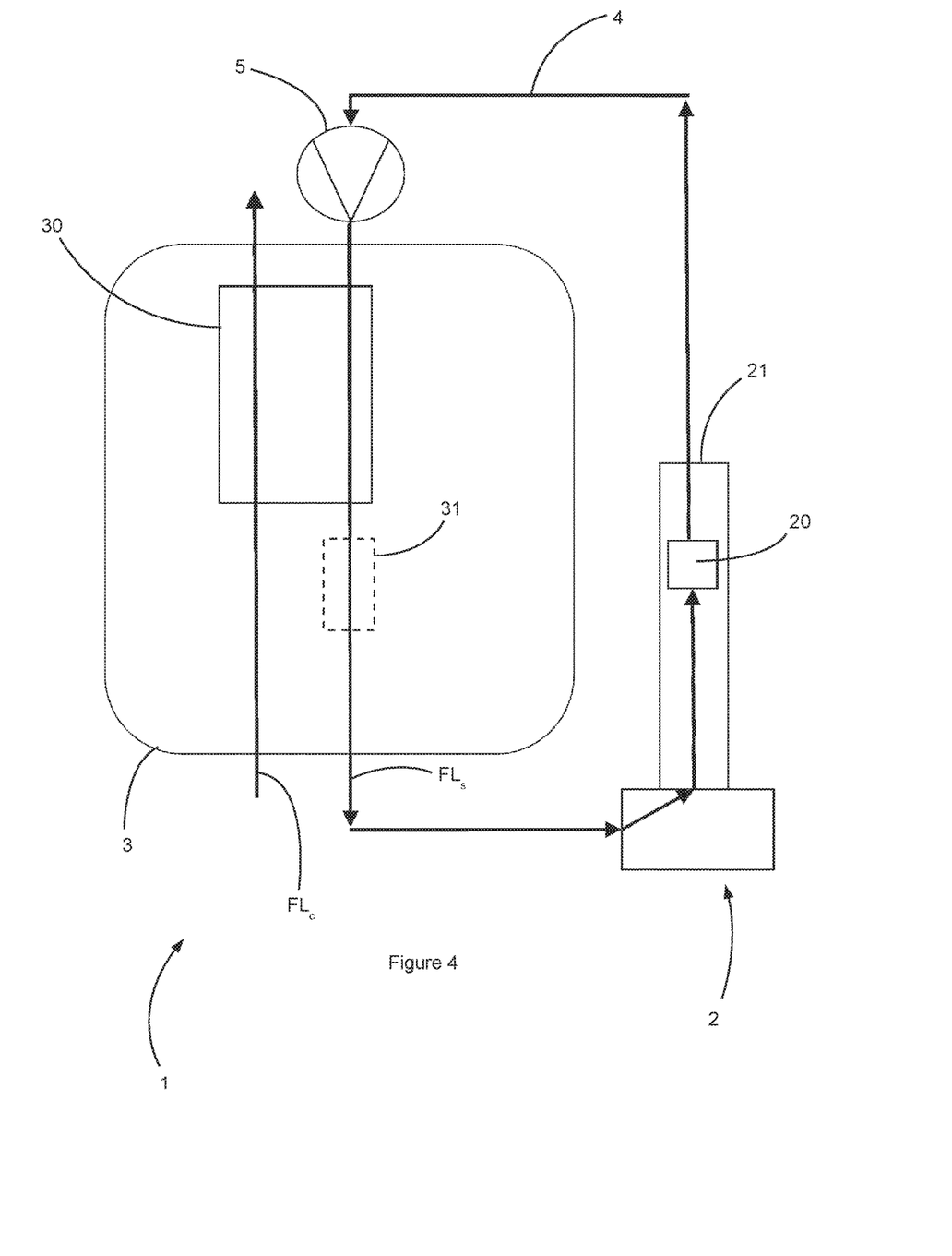
FIG. 4 depicts an NMR analysis system according to one particular embodiment designed to operate in accordance with FIG. 3.

FIG. 4 depicts a nuclear magnetic resonance (NMR) analysis system 1. According to a first embodiment of the invention, the system comprises:

a nuclear magnetic resonance analysis probe 2;

a device 3 for controlling the temperature of a flow of fluid intended to be used by the probe, referred to as "first flow";

a circuit 4 for circulating the first flow intended to be used by the probe;

a command module (not depicted).

The NMR analysis probe 2, depicted schematically in FIG. 4, comprises a sample holder 20 intended to contain a sample that is to be analysed. The sample holder 20 is incorporated into a rotor (not depicted) equipped for example with a turbine for spinning it. The rotor is placed inside a stator 21. The latter is itself situated, in a known way, at the magnetic centre of the complete NMR device.

The circulation circuit 4 is intended to cause a flow of a fluid, intended to be used by the probe 2, to circulate in a closed loop.

The fluid is, for example, helium or nitrogen. It comes from a source such as a standard container, for example a pressurized fluid cylinder. It is intended to be circulated through the circuit 4 in the form of a flow $FL_S$ intended to be used by the probe 2. This flow may have various functions within the probe 2. In the exemplary embodiment described here, it has the function of spinning the sample holder 20 and of raising/lowering the sample to a desired temperature for conducting an NMR analysis. This temperature is, for example, comprised between 8K and 300K. The sample holder 20 spun by the flow $FL_S$ has a rotational frequency that is dependent on the flow rate of the flow $FL_S$. The flow $FL_S$ can be divided in the probe in order to produce distinct flows respectively intended to perform the various functions.

The circulation circuit is designed so that the flow $FL_S$ passes through the control device 3 and the probe 2. It comprises a compression module 5 comprising at least one compressor of the compressor-pump type. This compression module 5 is arranged in the pressurized closed loop so as to circulate the flow $FL_S$ through this loop. In the exemplary embodiment described here, it is arranged between a flow outlet of the NMR analysis device and a flow inlet of the control device 3. However, it could be arranged in some different position along the circuit 4. It could notably be placed inside the cryostat 3.

The control device 3 is intended to control (namely set or regulate) the temperature of the first flow $FL_S$ so as to set the temperature of this first flow $FL_S$. In this instance it is a cryostat. In a first particular embodiment of the invention, the device 3 incorporates a heat exchanger 30. In this exemplary embodiment, the heat exchanger 30 is arranged in such a way as to perform an exchange of heat between a cooling flow, referred to as "second flow" and the first flow $FL_S$ intended for the probe 2. The cooling second flow, also referred to as cryogenic flow and denoted $FL_C$, comes from an external cryogenic fluid cold source (not depicted). In operation, it passes through the heat exchanger 30 at a given flow rate $D\_FL_C$ equal to or below a maximum flow rate $D_{max}\_FL_C$. The flows $FL_C$ and $FL_S$ are intended in this instance to pass through the heat exchanger 30 in opposite directions.

In another exemplary embodiment, the heat exchanger 30 is cooled by a cold-producing machine interposed between the downstream side of the exchanger and the upstream side of the probe (downstream and upstream referring to the direction in which the first flow $FL_S$ circulates). In such a case, there is no second flow $FL_C$.

The command module comprises a microprocessor and software elements designed to command the operation of the various elements of the NMR analysis system 1, notably the thermal control device 3. As an alternative, two command modules may be provided, one intended to command the operation of the probe and the other intended to command the circulation of the fluids $FL_C$ and $FL_S$ and the operation of the thermal control device. The command module or modules are designed to command the execution of the steps of the method of controlling the temperature of the first flow and the steps of the method of operating the NMR analysis system 1, which steps will be described hereinafter.

The method of operating the NMR analysis system 1 according to a first particular embodiment of the invention will now be described with reference to FIG. 5. This method of operation involves implementing a method of controlling the temperature of the first flow that is intended to be used by the probe $FL_S$, so as to spin a sample holder at a rotational frequency dependent on the flow rate of the flow $FL_S$ and to cool the sample, according to a first embodiment, as will become apparent from the description that follows.

Figure 2:
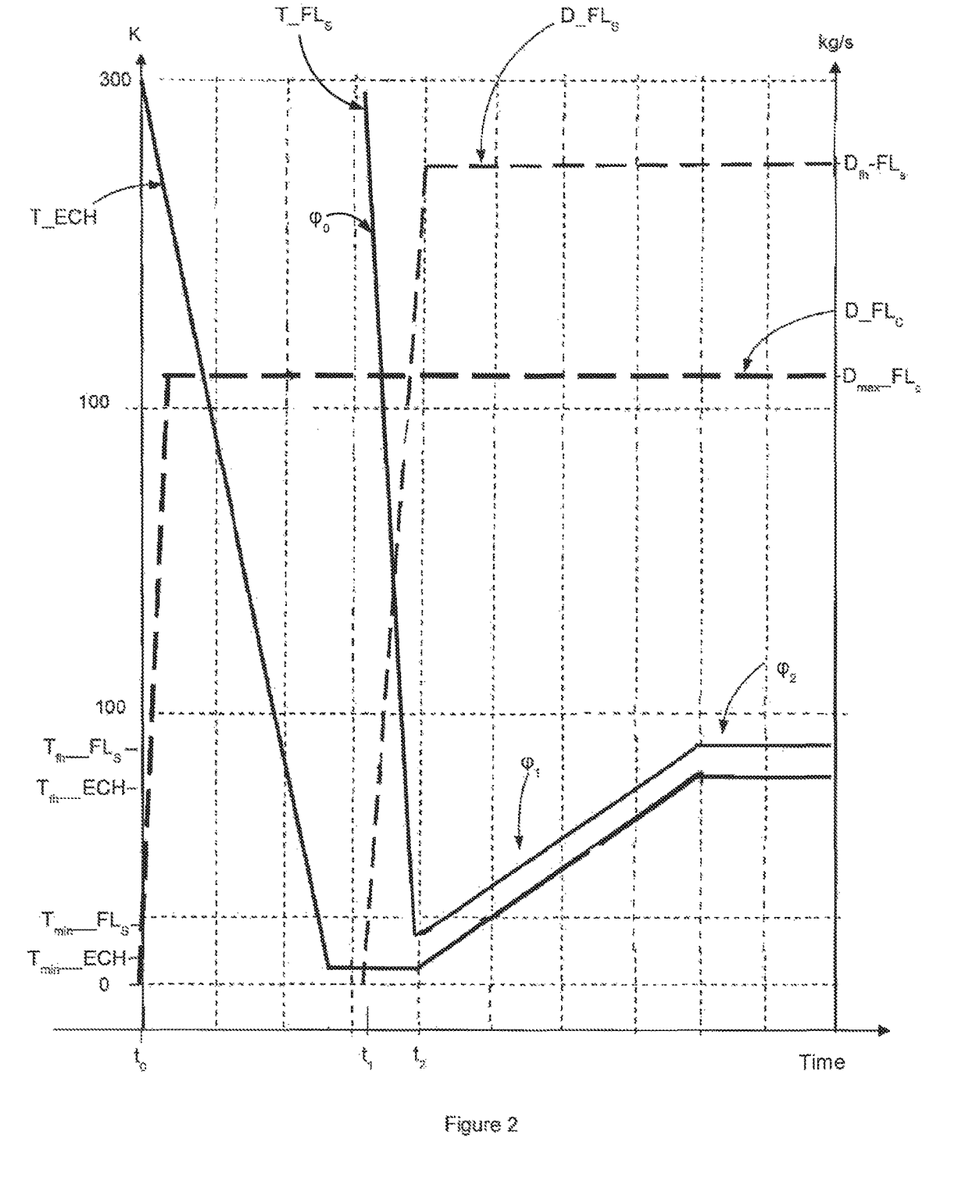
FIG. 2 depicts the evolutions with respect to time of various physical parameters (flow rates, temperatures) when implementing the method for controlling the temperature of the first flow intended for the NMR analysis probe during operation of the NMR analysis system according to a first particular embodiment of the invention.
Figure 5A:
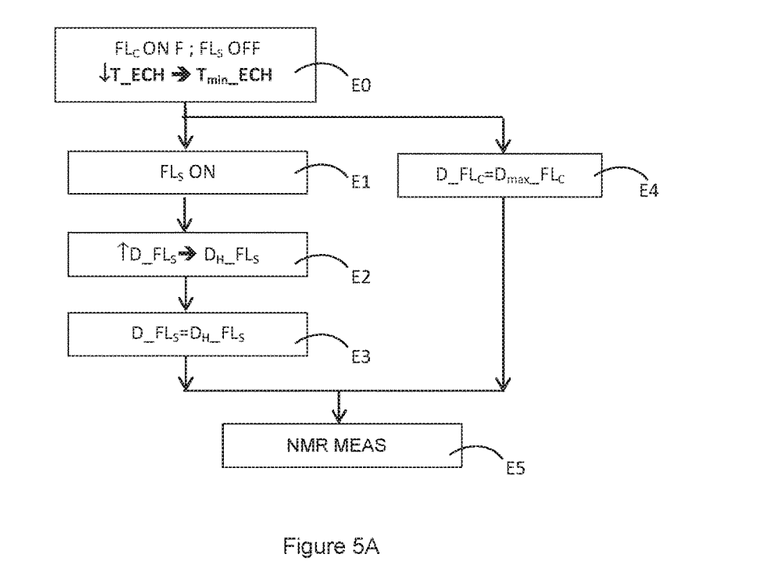
FIG. 5A depicts a flow diagram of the steps of the method of operation of the NMR analysis system incorporating a method for controlling the temperature of the first flow corresponding to FIG. 2.

With reference to FIGS. 2 and 5A, the method of operating the NMR analysis system 1 comprises an initial step E0 of lowering the temperature T_ECH of the heat exchanger.

The temperature of the exchanger is measured by one or more probes placed on or in the body of the exchanger 30. There is no need to measure the absolute value of the temperature T_ECH. All that is required here is to measure a variation in this temperature T_ECH so as to monitor how it evolves with respect to time. It is for example possible to make a spot measurement of the temperature and/or to determine a mean temperature from a number of measurement points.

The step E0 consists in circulating the cryogenic flow $FL_C$ through the exchanger 30 but in this instance without circulating the first flow $FL_S$ intended for the probe. In other words, the initial flow rate of the first flow is equal to zero: $D\_FL_S=0$. Initially, at an instant $t_0$, the flow rate of the cryogenic flow, or second flow, denoted $D\_FL_C$, is zero. During the step E0, from this instant $t_0$ on, the circulation of the cryogenic fluid $FL_C$ is initiated and its flow rate $D\_FL_C$ passes rapidly from zero to a desired value, for example equal to the maximum flow rate of the fluid $FL_C$ (namely the highest flow rate at which this fluid can circulate through the exchanger 30), denoted $D_{max}\_FL_C$. During the step E0, the exchanger 30 therefore operates with the cryogenic second fluid $FL_C$ circulating, but without the circulation of the first flow $FL_S$. This results in a drop in the temperature of the exchanger T_ECH until it reaches a desired low value. This value may correspond to a stable (or equilibrium) minimum temperature $T_{min}\_ECH$ of the heat exchanger 30 through which only the cryogenic flow $FL_C$ passes. However, it is possible for the temperature of the exchanger 30 not to be decreased down to the minimum equilibrium temperature $T_{min}\_ECH$. The temperature of the exchanger 30 could, for example, be lowered to a low temperature chosen according to an end-application. In any event, during the initial cooling step the temperature of the heat exchanger 30 is advantageously lowered to a low value which is below an equilibrium value $T_{fn}\_ECH$ that will be reached later after the first flow $FL_S$ has circulated with an operational flow rate or "first flow rate".

After the temperature of the exchanger 30 has reached the desired low value (here $T_{min}\_ECH$), the initial step E0 may be continued for a short length of time in order temporarily to maintain the low temperature (in this instance $T_{min}\_ECH$) of the exchanger 30 while waiting to initiate the next step E1.

In one particular alternative form of embodiment, the initial step E0 of cooling the exchanger 30 is performed with the first flow $FL_S$ circulating but at a low flow rate $D\_FL_S$. For example, the flow rate $D\_FL_S$ is set to a low value allowing the circuit 4 to be placed at a slight overpressure with respect to the outside thus avoiding the ingress of external contaminants.

Because the heat exchanger 30 has a certain mass, of the order of several tens of kilograms, this initial, or prior, cooling step E0 allows the exchanger 30 to be "charged" with frigories. At the end of the step E0, the exchanger 30 constitutes a reservoir of thermal energy, of the cold reservoir type. Because the exchanger 30 has a certain thermal inertia, this reservoir can be used subsequent to step E0 to accentuate the cooling of the first flow intended for the probe $FL_S$, as will become apparent in the description that follows.

At the end of the step E0, at an instant $t_1$, the command module initiates a circulation of the first flow of fluid $FL_S$ intended to be used by the probe 2, during a step E1.

During a step E2, the flow rate of the first flow intended for the probe $FL_S$, zero prior to the instant $t_1$, is rapidly increased and set to a fixed first flow rate strictly higher than zero and constituting an operational flow rate. This set first flow rate denoted $D_{fh}\_FL_S$, here is set to cause the sample holder 20 to spin at a high rotational frequency "$f_h$", for example in excess of 10 Hz, for example again comprised between 10 and 20 kHz. The first flow rate of the first flow $FL_S$ is thus set to a value corresponding to a frequency higher than or equal to a limit rotational frequency (this limit frequency being for example equal to 10 kHz). By definition, the limit rotational frequency is the rotational frequency reached when the exchanger 30 is temperature stabilized for this rotational frequency without implementation of the invention (and therefore without the initial step E0). The high flow rate $D_{fh}\_FL_S$ therefore corresponds to a high rotational frequency "$f_h$" of the probe 2.

Circulation of the first flow $FL_S$ in the circuit 4 is then maintained, at a stable flow rate equal to $D_{fh}\_FL_S$, during a step E3.

Let us note that, following the step E0 and simultaneously with steps E1 et seq, the circulation of the second flow $FL_S$ through the exchanger 30 at a flow rate here equal to $D_{max}\_FL_C$ is maintained, as represented by step E4 in FIG. 5A.

As circulation of the first flow $FL_S$ at the set flow rate, here equal to $D_{fh}\_FL_S$, is established by executing steps E0 to E4, the temperature of the flow $FL_S$ is controlled, or regulated, by the control device 3, notably by passing through the heat exchanger 30. This results in an evolution with respect to time of the temperature of the first flow $FL_S$ which comprises three successive phases $\varphi_0$, $\varphi_1$ and $\varphi_2$, described hereinafter.

The first phase, or initial phase $\varphi_0$, is a cooling phase during which the temperature of the first flow $FL_S$ drops progressively to a low value as depicted in FIG. 2. During this initial phase $\varphi_0$, the cooling of the first flow $FL_S$ passing through the exchanger 30 is brought about by two types of heat transfer comprising:

in the conventional way, an exchange of heat between the first flow $FL_S$ and the second flow $FL_C$, the two flows circulating through the exchanger 30 (in this instance in opposite directions), and according to the invention, a transfer of heat between the heat exchanger 30, previously cooled and acting as a cold reservoir, and the flow $FL_S$.

Thanks to the thermal inertia of the previously-cooled exchanger 30, the first flow $FL_S$ intended for the probe drops to a temperature far lower than it would have reached in conventional operation of the exchanger 3 consisting in initiating circulation of each of the first and second fluids $FL_S$ and $FL_C$ substantially at the same time, without the preliminary step E0 of cooling the heat exchanger 30. In the example described here, during the initial phase of cooling the flow $FL_S$, the heat exchanger 30 supplies a thermal power of the order of 2 kW.

The cooling phase $\varphi_0$ finishes when the thermal energy accumulated in the mass of the heat exchanger 30 is spent. It is followed by a second phase referred to as a transient phase $\varphi_1$ which involves a raising of the temperature of the first flow $FL_S$ to an equilibrium value denoted $T_{ph\_}FL_S$. In parallel, the temperature of the exchanger T_ECH also rises during the transient phase $\varphi_1$, to an equilibrium value denoted $T_{ph\_}$ECH.

The transient phase $\varphi_1$ is followed by a third phase referred to as an equilibrium phase $\varphi_2$, during which the temperature of the first flow $FL_S$ remains stable and equal to the value $T_{ph\_}FL_S$. In parallel, the temperature of the exchanger T_ECH also stabilizes at the equilibrium value $T_{ph\_}$ECH. The equilibrium phase $\varphi_2$ is thus characterized by a first temperature plateau for the flow $FL_S$ at the value $T_{ph\_}FL_S$ and by a second temperature plateau of the exchanger at the value $T_{ph\_}$ECH. These two temperature plateaus correspond to thermal equilibrium between the first and second flows $FL_S$ and $FL_C$ circulating at respective flow rates $D_{max\_}FL_C$ and $D_{ph\_}FL_S$ through the heat exchanger 30. Remember that the flow rate $D_{ph\_}FL_S$ corresponds to a high rotational frequency of the sample holder 20 of the probe 2.

During the transient phase $\varphi_1$, the temperature of the first flow $FL_S$ passes through a range of temperatures, here comprised between $T_{min\_}FL_S$ and $T_{ph\_}FL_S$. This range of temperatures is situated below the equilibrium temperature $T_{ph\_}FL_S$ which corresponds to a high rotational frequency $f_h$ of the probe even though the flow rate of the first flow $FL_S$ is already high (here equal to $D_{ph\_}FL_S$) and therefore causes the sample holder 20 of the probe 2 to spin at the high rotational frequency $f_h$.

The transient phase $\varphi_1$ is of a duration that is set in such a way as to allow the probe 2 to create an NMR spectrum of a sample.

According to the first embodiment of the invention, the probe 2 creates an NMR spectrum of a sample during this transient phase $\varphi_1$, during an NMR analysis step E5. Indeed the NMR measurement may be able to cope with a variation for example of a few degrees K per minute (for example 5K/min).

The invention has another advantage: it allows probe temperature fluctuations to be decreased (both in amplitude and in frequency) thereby stabilizing the speed at which the sample holder spins because the thermal inertia (or specific heat) of the material of which the heat exchanger is made is far higher than the thermal inertial (or specific heat) of the gas. For example:

at 20K, the specific heat of the exchanger material is of the order of twice that of He (helium);

at 40K, the specific heat of the exchanger material is of the order of 10 times that of He;

at 60K, the specific heat of the exchanger material is of the order of 25 times that of He.

The steps E0 to E5 are executed at the command of the command module(s).

Note that the temperature of the first flow $FL_S$ intended to be used by the probe 2 is controlled or regulated by a control method which comprises steps E0 to E4 and phases $\varphi_0$ to $\varphi_2$. This method for controlling or regulating the temperature of the first flow $FL_S$ forms part of the method for operating the NMR analysis system. The method for operating the probe 2 according to the first embodiment comprises steps E0 to E5 and phases $\varphi_0$, $\varphi_1$, $\varphi_2$.

Figure 3:
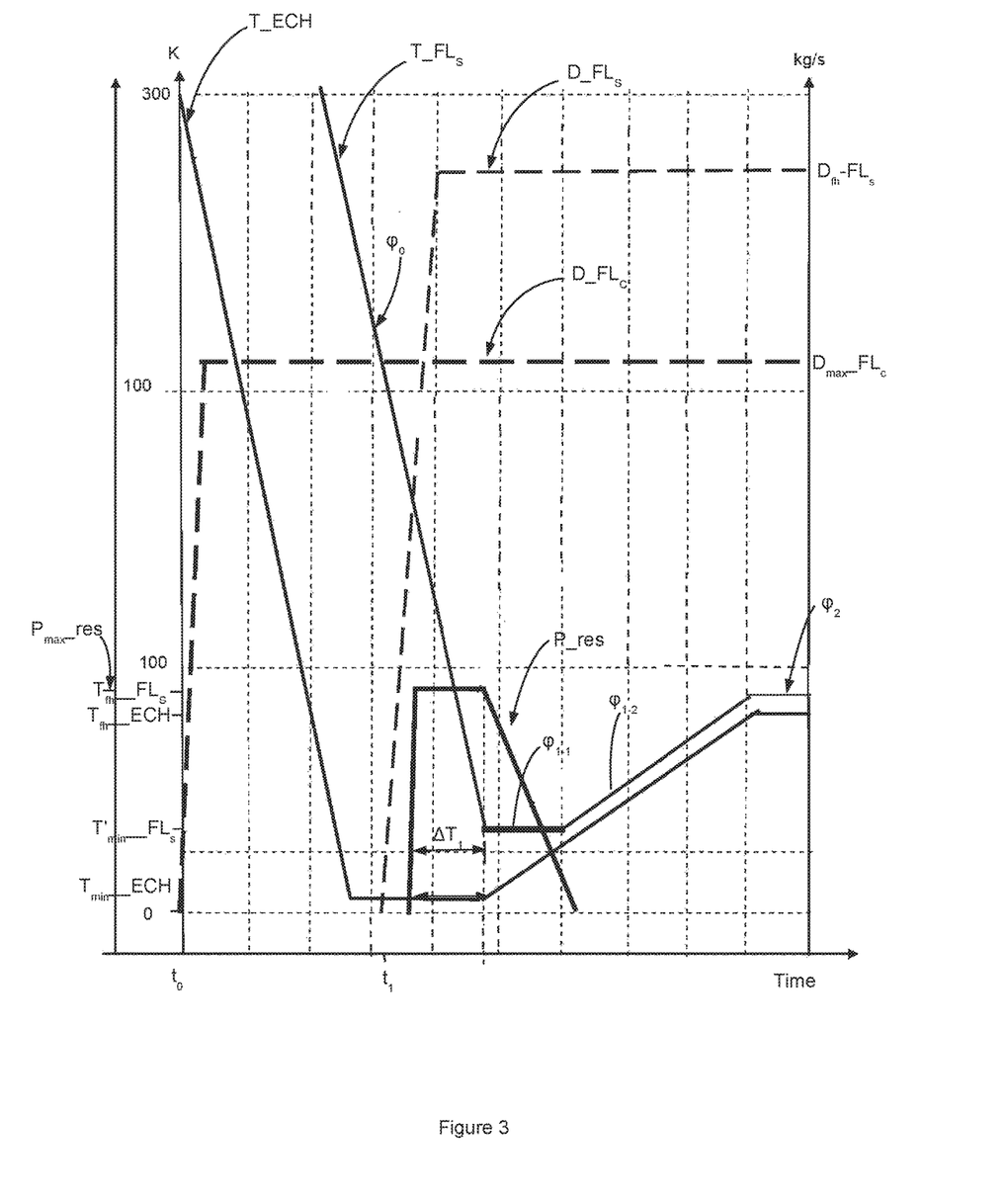
FIG. 3 depicts the evolutions with respect to time of various physical parameters (flow rates, temperatures) when implementing the method for controlling the temperature of the first flow intended for the NMR analysis probe during operation of the NMR analysis system according to a second particular embodiment of the invention.

A second embodiment of the method for controlling or regulating the temperature of the first flow $FL_S$ intended to be used by the NMR probe 2 and the method for operating the NMR analysis system 1 will now be described with reference to FIGS. 3 and 5B. For the sake of clarity, only elements of this second embodiment which differ from the first embodiment will be described in detail.

To implement this second embodiment, the control device 3 comprises, in addition to the heat exchanger 30, a heating module 31 depicted in dotted line in FIG. 4. The device 3 here is a cryostat. The heating module 31 comprises, for example, an electrical resistance. The circuit for circulating the first flow $FL_S$ passes not only through the heat exchanger 30 but also through the heating module 31. In the example described here, the heating module 31 is placed downstream of the heat exchanger 30 in the direction in which the first flow $FL_S$ circulates. It is operated by the command module. The thermal heating power supplied by the heating module 31 can be set and adjusted so as to contribute to setting the temperature of the first flow $FL_S$, as will become apparent in the following description of the method for controlling the temperature of the flow $FL_S$ which follows.

Figure 5B:
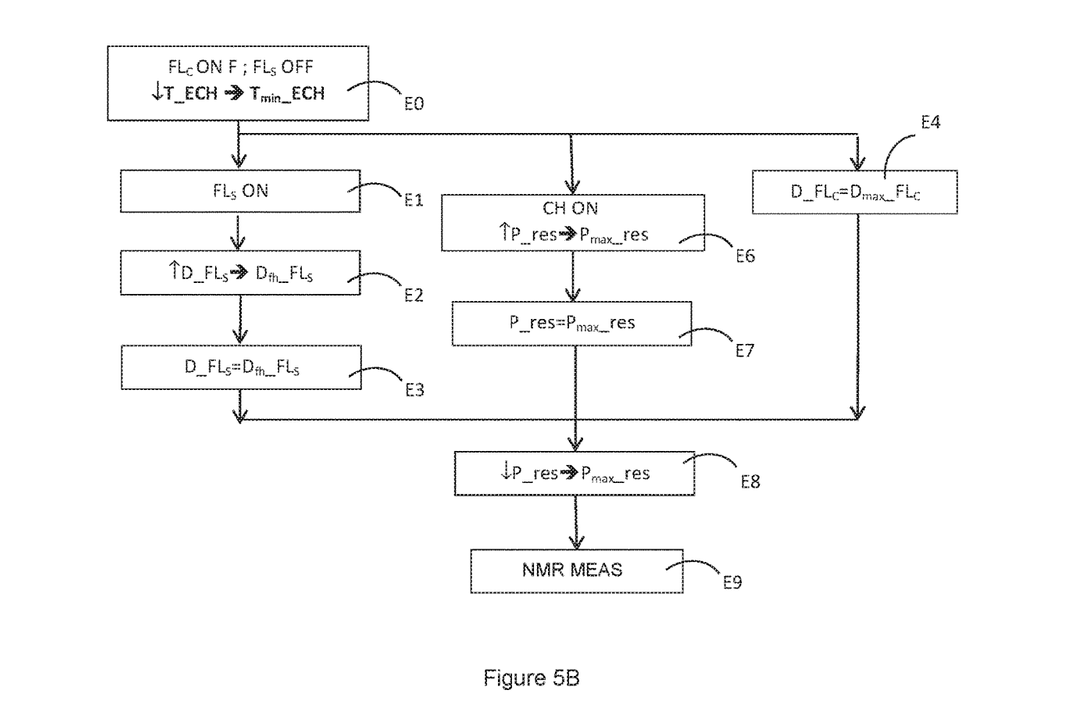
FIG. 5B depicts a flow diagram of the steps of the method of operation of the NMR analysis system incorporating a method for controlling the temperature of the first flow corresponding to FIG. 3.

With reference to FIG. 5B, the control method comprises an initial step E0 of cooling the heat exchanger 30, here without the circulation of the first flow $FL_S$. In other words, the initial flow rate of the first flow $FL_S$ is equal to zero: $D\_FL_S=0$. During the step E0, the second flow $FL_S$ circulates at a flow rate here at the maximum flow rate $D_{max\_}FL_C$. The initial step E0 is followed by a step E1 of initiating circulation of the first flow $FL_S$ then by a step E2 of setting the flow rate of the flow $D\_FL_S$ to a first flow rate strictly higher than zero. This first flow rate, denoted $D_{ph\_}FL_S$, here corresponds to a high rotational frequency $f_h$ of the probe 2. Next, the method comprises a step E3 of circulating the flow $FL_S$ at the fixed first flow rate $D_{ph\_}FL_S$.

According to the second embodiment of the invention, the first flow $FL_S$ circulating at the first flow rate passes through the heating module 31, in this instance after having passed through the heat exchanger 30. To start with (namely from the initial instant $t_0$ onwards), the heating module 31 here is switched off, the thermal heating power supplied being zero. During a step E6 (FIG. 5B), the thermal power of the thermal heating module 31, denoted P_res, is increased sharply until it reaches a high power level. In other words, the heating power of the module 31 is raised to a high value. This high level of power is in this instance kept stable for a short period of time $\Delta T1$, during a step E7, and thus forms a power plateau as depicted in FIG. 3. Here it corresponds to the maximum thermal power $P_{max}\_res$ that the thermal resistance can supply. This thermal power $P_{max}\_res$ here is of the order of a few hundred watts. Step E6 here is initiated slightly after the circulation of the first flow $FL_S$ is initiated during step E2.

As an alternative, step E6 could be initiated simultaneously with step E2 or substantially before the latter. It is also possible to conceive of rising the thermal heating power P_res to the desired plateau value, in this instance $P_{max}\_res$, at any time prior to the step E1 of triggering the circulation of the flow $FL_S$.

Steps E6 and E7 are advantageously executed in such a way that the thermal power supplied by the heating module 31 is at a maximum substantially at the start of or shortly after the start of the step E3 of circulating the flow $FL_S$ at the set fixed flow rate (here $D_{fh}\_FL_S$).

Step E7 is followed by a step E8 of lowering the thermal heating power supplied by the heating module 31. During this step E8, the heating module 31 (in this instance the electrical resistance) is operated in such a way as to reduce the thermal heating power P_res in order to lower it from $P_{max}\_res$ to zero.

Thus, the first flow $FL_S$ circulating at the first flow rate is first of all cooled by passing through the heat exchanger 30 down to a very low temperature, in this instance $T'_{min}\_FL_S$, then heated up slightly as it passes through the heating module 31, the power of which has been raised to $P_{max}\_res$. In the example described here, the exchanger 30 provides a power of the order of 2 kW whereas the heating module 31 supplies a few hundred watts. The reduction in thermal heating power P_res from the high power level (in this instance $P_{max}\_res$) is adjusted or set so that the temperature of the flow $FL_S$ intended for the probe is temporarily stable and equal to $T'_{min}\_FL_S$ for part of the transient phase $\varphi_1$, in this instance for a first part of the transient phase. The command module thus operates the heating module 31 in such a way that the thermal heating power supplied is at a maximum just after circulation of the said flow $FL_S$ intended for the probe is initiated and then decreases in a way that is set so that the temperature of the flow $FL_S$ intended for the probe 2 is temporarily stable.

The way in which the temperature of the first flow $FL_S$ intended for the probe 2 evolves with respect to time comprises, as in the first embodiment, the following three successive phases:
- a phase $\varphi_0$ of cooling the temperature;
- a transient phase $\varphi_1$, involving a rise in temperature;
- an equilibrium phase $\varphi_2$, during which the temperature remains stable and equal to an equilibrium value.

These phases $\varphi_0$, $\varphi_1$, $\varphi_2$ are analogous to those of the first embodiment described but differ therefrom in the following respect:
- the low value of the temperature reached at the end of the cooling phase $\varphi_0$, $T'_{min}\_FL_S$, according to the second embodiment, is slightly higher than the low value $T_{min}\_FL_S$ reached at the end of the phase $\varphi_0$ according to the first embodiment;
- the transient phase $\varphi_1$ comprises a stable temperature plateau (denoted $\varphi_{1\_1}$) here equal to the minimum temperature $T'_{min}\_FL_S$, prior to a rise (denoted $\varphi_{1\_2}$) in the temperature $T\_FL_S$ of the first flow $FL_S$ so as far as the equilibrium temperature $T_{fh}\_FL_S$.

In the embodiment described here, the thermal plateau relating to the first flow $FL_S$ during the transient phase $\varphi_1$ is situated in the first part of this transient phase $\varphi_1$ which causes the temperature of the first flow $FL_S$ to move from the lowest value achieved $T'_{min}\_FL_S$ to the equilibrium value $T_{fh}\_FL_S$. As an alternative, it might be possible to consider the thermal plateau being situated subsequently in the transient phase $\varphi_1$ after a first rise in temperature $T\_FL_S$ and before a second rise in temperature $T\_FL_S$ to the equilibrium temperature $T_{fh}\_FL_S$.

Let us emphasise that, during the transient phase $\varphi_1$, and notably during the thermal plateau relating to the temperature $T\_FL_S$, the temperature of the first flow $FL_S$, here equal to the value $T_{min}\_FL_S$, is lower than the equilibrium temperature $T_{fh}\_FL_S$ (corresponding to a high rotational frequency $f_h$ of the probe 2) even though the flow rate of the first flow $FL_S$ has already been set to the desired value (or first flow rate) here equal to $D_{fh}\_FL_S$, and therefore causes the sample holder 20 of the probe 2 to spin at the desired rotational frequency, in this instance a high frequency $f_h$.

According to the second embodiment of the invention, the probe 2 creates an NMR spectrum of a sample during the thermal plateau relating to the first flow $FL_S$ created during the transient phase $\varphi_1$, in an NMR analysis step E9.

The method of controlling the temperature of the first flow $FL_S$ according to the second embodiment comprises the steps E0-E4 and E6-E8 and the phases $\varphi_0$, $\varphi_1$, $\varphi_2$ which have just been described with reference to FIGS. 3 and 5B. The method of operating the probe 2 according to the second embodiment comprises the steps E0-E4 and E6-E8, phases $\varphi_0$, $\varphi_1$, $\varphi_2$ and the analysis step E9.

In the two embodiments that have just been described with reference to FIGS. 2, 5A and 3, 5B, during the initial step E0 of cooling the exchanger there is no circulation of the first flow $FL_S$. In other words, the initial flow rate of the flow $FL_S$ is zero. As an alternative, during the initial step E0, the first flow $FL_S$ could be circulated at an initial flow rate $D_0\_FL_S$ strictly lower than the first flow rate (which is for example equal to the flow rate $D_{fh}\_FL_S$) set subsequently to the initial step E0. The initial flow rate $D_0\_FL_S$ of the first flow $FL_S$ may notably be set to a value that is set in such a way that the pressure inside the circuit 4 in which the flow $FL_S$ circulates is higher than or equal to the ambient pressure of this circuit 4 (i.e. greater than or equal to the pressure outside the circuit).

The invention claimed is:

1. A method for controlling the temperature of a first flow of fluid ($FL_S$) intended to be used by a nuclear magnetic resonance analysis probe to spin a sample holder of the probe at a given rotational frequency dependent on a flow rate of the flow, comprising:
   circulating the first flow, during which circulation the first flow ($FL_S$) passes through a heat exchanger at a first flow rate, and
   in an initial cooling, lowering a temperature (T_ECH) of the heat exchanger and, at the same time, setting the flow rate of the first flow ($FL_S$) to an initial flow rate which is lower than the first flow rate,
   wherein the circulating of the first flow ($FL_S$) at the first flow rate is initiated following the initial cooling.

2. The method according to claim 1, wherein the initial flow rate of the first flow is set to zero.

3. The method according to claim 1, wherein, while the first flow ($FL_S$) circulates through a circuit, the initial flow rate of the first flow ($FL_S$) is set to a value so that a pressure inside the circuit is greater than or equal to a pressure outside the circuit.

4. The method according to claim 1, wherein, during the initial cooling, the temperature of the heat exchanger is lowered to a low value which is lower than an equilibrium value Tfh_ECH reached after the intended first flow circulation at the first flow rate.

5. The method according to claim 1, wherein, during the initial cooling, a second flow ($FL_C$) of a coolant is circulated through the heat exchanger at a flow rate ($D_{max}\_FL_C$) which is a maximum flow rate of the cooling flow ($FL_C$).

6. The method according to claim 5, wherein, during the initial cooling, the temperature (T_ECH) of the exchanger is lowered to a low value ($T_{min}\_FL_S$) which corresponds to a minimum equilibrium temperature of the heat exchanger through which the second cooling flow ($FL_C$) passes.

7. The method according to claim 1, wherein, following triggering of the circulating of the first flow, while the first flow rate ($D\_FL_S$) of the first flow is set to a desired value, an evolution of the temperature ($T\_FL_S$) of the first flow ($FL_S$) with respect to time comprises in succession (i) a first phase ($\varphi_0$) of lowering the temperature, (ii) a transient second phase ($\varphi_1$) comprising raising the temperature to an equilibrium value, and (iii) an equilibrium third phase ($\varphi_2$) in which the temperature is stable and equal to the equilibrium value, the transient phase being of a duration that is set so as to allow the probe to create an NMR spectrum of a sample.

8. The method according to claim 7, wherein the first flow ($FL_S$), circulating at the first flow rate, passes through a heating module, and wherein the heating power of the module is raised to a high value then decreased so that the temperature ($T\_FL_S$) of the first flow ($FL_S$) is temporarily stable for part of the transient phase ($\varphi_1$).

9. The method according to claim 8, wherein the circulating first flow ($FL_S$) passes through the heating module downstream of the heat exchanger in the direction in which the flow ($FL_S$) circulates.

10. The method according to claim 8, wherein the heating module comprises an electrical resistance.

11. The method according to claim 10, wherein the first flow rate of the first flow is set to a value corresponding to a frequency greater than or equal to a limit rotational frequency.

12. The method of operating a nuclear magnetic resonance analysis system comprising a probe for nuclear magnetic resonance analysis of a sample, a circuit for circulating a first flow of fluid ($FL_S$) intended to be used by the probe, and a device for controlling the temperature of the first flow ($FL_S$) comprising a heat exchanger, said method comprising:
controlling a temperature of the first flow ($FL_S$) by the control device implementing the control method according to claim 1.

13. The method according to claim 12,
wherein, following triggering of the circulating of the first flow, while the first flow rate ($D\_FL_S$) of the first flow is set to a desired value, an evolution of the temperature ($T\_FL_S$) of the first flow ($FL_S$) with respect to time comprises in succession (i) a first phase ($\varphi_0$) of lowering the temperature, (ii) a transient second phase ($\varphi_1$) comprising raising the temperature to an equilibrium value, and (iii) an equilibrium third phase ($\varphi_2$) in which the temperature is stable and equal to the equilibrium value, the transient phase being of a duration that is set so as to allow the probe to create an NMR spectrum of a sample,
and wherein the probe creates an NMR spectrum of a sample during the transient phase ($\varphi_1$).

14. The method according to claim 12,
wherein, following triggering of the circulating of the first flow, while the first flow rate ($D\_FL_S$) of the first flow is set to a desired value, an evolution of the temperature ($T\_FL_S$) of the first flow ($FL_S$) with respect to time comprises in succession (i) a first phase ($\varphi_0$) of lowering the temperature, (ii) a transient second phase ($\varphi_1$) comprising raising the temperature to an equilibrium value, and (iii) an equilibrium third phase ($\varphi_2$) in which the temperature is stable and equal to the equilibrium value, the transient phase being of a duration that is set so as to allow the probe to create an NMR spectrum of a sample,
wherein the first flow ($FL_S$), circulating at the first flow rate, passes through a heating module, and wherein the heating power of the module is raised to a high value then decreased so that the temperature ($T\_FL_S$) of the first flow ($FL_S$) is temporarily stable for part of the transient phase ($\varphi_1$)
and wherein the probe creates an NMR spectrum of a sample when the temperature ($T\_FL_S$) of the first flow ($FL_S$) is temporarily stable during part of the transient phase ($\varphi_1$).

15. A device for controlling a temperature of a first flow of a fluid intended to be used by a nuclear magnetic resonance analysis probe to spin a sample holder of the probe at a given rotational frequency dependent on a flow rate of the flow, the device comprising:
at least one heat exchanger through which the first flow ($FL_S$) is intended to circulate at a first flow rate, and
a command module designed to command an initial drop in a temperature (T_ECH) of the heat exchanger and at the same time set the flow rate of the first flow to an initial flow rate lower than the first flow rate, then initiate circulation of the first flow ($FL_S$) through the exchanger at the first flow rate.

16. The device according to claim 15, wherein the command module is designed to set the initial flow rate to zero.

17. The device according to claim 15, wherein, while the first flow ($FL_S$) is circulating through a circuit, the command module is designed to set the initial flow rate of the said first flow ($FL_S$) to a value that is set so that the pressure inside the circuit is greater than or equal to the pressure outside the circuit.

18. The device according to claim 15, wherein the heat exchanger is designed to have passing through it a second flow ($FL_C$) of a coolant, and wherein the command module is designed to initially command the cooling second flow ($FL_C$) to circulate at a flow rate which is a maximum flow rate ($D_{max}\_FL_C$) of the cooling flow ($FL_C$), so as to obtain the initial drop in temperature of the exchanger.

19. The device according to claim 18, wherein the command module is designed to command an initial drop in the temperature of the exchanger down to a low value ($T_{min}\_ECH$) which corresponds to a minimum equilibrium temperature of the heat exchanger through which the second flow ($FL_C$) passes, before initiating the circulation of the first flow ($FL_C$) at the first flow rate.

20. The device according to claim 15, comprising a heating module supplying a thermal power to the first flow ($FL_S$) and wherein the command module is designed to operate the heating module so that the thermal power provided is at a maximum after the initiation of the circulation of the first flow ($FL_S$) at the first flow rate and then decreases in a suitable way so that the temperature ($T\_FL_S$) of the first flow ($FL_S$) is temporarily stable.

21. The device according to claim 20, wherein the heating module is positioned downstream of the heat exchanger in the direction of circulation of the first flow ($FL_S$).

22. The device according to claim 20, wherein the heating module comprises an electrical resistance.

23. A nuclear magnetic resonance analysis system, comprising:
- a probe for nuclear magnetic resonance analysis of a sample,
- a circuit for the circulation of a first flow of fluid $FL_S$ intended to be used by the probe to spin a sample holder of the probe at a given rotational frequency dependent on a flow rate of the flow, and
- a device for controlling the temperature of the first flow according to claim 15.

24. The system according to claim 23, comprising a command module designed to command the creation of a spectrum by the probe after the circulation of the first flow at the first flow rate has been initiated, during a transient phase ($\varphi_1$) subsequent to an initial drop in the temperature ($T\_FL_S$) of the first flow ($FL_S$) to a low value ($T_{min}\_FL_S$; $T'_{min}\_FL_S$) and prior to a phase ($\varphi_2$) of equilibrium of the temperature ($T\_FL_S$) of the flow intended for the probe at a value higher than the low value.

25. The system according to claim 24,
- wherein the device for controlling the temperature of the first flow comprises a heating module supplying a thermal power to the first flow ($FL_S$),
- wherein the command module is designed to operate the heating module so that the thermal power provided is at a maximum after the initiation of the circulation of the first flow ($FL_S$) at the first flow rate and then decreases in a suitable way so that the temperature ($T\_FL_S$) of the first flow ($FL_S$) is temporarily stable, and
- wherein the command module is designed to command the creation of a spectrum by the probe when the temperature of the first flow is temporarily stable ($T'_{min}\_FL_S$) during the transient phase ($\varphi_1$).

* * * * *